United States Patent
Lee et al.

(10) Patent No.: US 10,335,710 B2
(45) Date of Patent: Jul. 2, 2019

(54) METHOD FOR PRODUCING ANHYDROUS SUGAR ALCOHOL USING AZEOTROPIC DISTILLATION

(71) Applicant: SK Innovation Co., Ltd., Seoul (KR)

(72) Inventors: Sang Il Lee, Daejeon (KR); Sung Real Son, Daejeon (KR); Young Bo Choi, Seoul (KR)

(73) Assignee: SK Innovation Co., Ltd., Seoul (KR)

( * ) Notice: Subject to any disclaimer, the term of this patent is extended or adjusted under 35 U.S.C. 154(b) by 86 days.

(21) Appl. No.: 15/518,827

(22) PCT Filed: Oct. 7, 2015

(86) PCT No.: PCT/KR2015/010588
§ 371 (c)(1),
(2) Date: Apr. 13, 2017

(87) PCT Pub. No.: WO2016/060399
PCT Pub. Date: Apr. 21, 2016

(65) Prior Publication Data
US 2017/0252669 A1 Sep. 7, 2017

(30) Foreign Application Priority Data
Oct. 16, 2014 (KR) .................. 10-2014-0139663

(51) Int. Cl.
*B01D 3/36* (2006.01)
*C07B 63/02* (2006.01)
*C07D 493/04* (2006.01)
*B01D 3/00* (2006.01)
*B01D 3/10* (2006.01)
*B01D 3/14* (2006.01)
*B01J 31/02* (2006.01)

(52) U.S. Cl.
CPC .............. *B01D 3/36* (2013.01); *B01D 3/002* (2013.01); *B01D 3/106* (2013.01); *B01D 3/143* (2013.01); *B01J 31/02* (2013.01); *C07B 63/02* (2013.01); *C07D 493/04* (2013.01)

(58) Field of Classification Search
CPC ........ B01D 3/002; B01D 3/106; B01D 3/143; B01D 3/36; B01J 31/02; C07B 63/02; C07D 493/04
See application file for complete search history.

(56) References Cited

U.S. PATENT DOCUMENTS

| 6,639,067 | B1 | 10/2003 | Brinegar et al. |
| 7,649,099 | B2 | 1/2010 | Holladay et al. |
| 7,893,194 | B2 | 2/2011 | van Walsem et al. |

FOREIGN PATENT DOCUMENTS

| JP | 4945447 B2 | 6/2012 |
| KR | 20010079763 A | 8/2001 |
| KR | 1020140059904 A | 5/2014 |
| KR | 1020140105193 A | 9/2014 |

OTHER PUBLICATIONS

Zhang, J, et al., Enhanced catalytic performance in dehydration of sorbitol to isosorbide over a superhydrophobic mesoporous acid catalyst, 2015, Catalysis Today 242, p. 249-254 (Year: 2015).*
Song; "Study on Collecting of Tetrahydrofuran by mixed solvent in azeotropic mixture"; Graduate School of Dong-A University, Department of Chemical Engineering; Master's Thesis; 2010; English-language Abstract.

* cited by examiner

*Primary Examiner* — Renee Robinson
*Assistant Examiner* — Derek N Mueller
(74) *Attorney, Agent, or Firm* — The Webb Law Firm

(57) ABSTRACT

The present invention relates to a method for producing anhydrosugar alcohol, and more particularly to a method of producing anhydrosugar alcohol using a solvent including at least two components that form an azeotrope with water at atmospheric pressure and that have significantly different boiling points. The method for producing anhydrosugar alcohol according to the present invention can increase the yield of anhydrosugar alcohol by efficiently controlling the reaction temperature by use of a solvent including at least two components that form an azeotrope with water at atmospheric pressure and that have significantly different boiling points.

14 Claims, No Drawings

METHOD FOR PRODUCING ANHYDROUS SUGAR ALCOHOL USING AZEOTROPIC DISTILLATION

CROSS-REFERENCE TO RELATED APPLICATIONS

This application is the U.S. national phase of International Application No. PCT/KR2015/010588 filed Oct. 7, 2015, and claims priority to Korean Patent Application No. 10-2014-0139663 filed Oct. 16, 2014, the disclosures of which are hereby incorporated in their entirety by reference.

TECHNICAL FIELD

The present invention relates to a method for producing anhydrosugar alcohol, and more particularly to a method of producing anhydrosugar alcohol using a solvent comprising at least two components that form an azeotrope with water at atmospheric pressure and that have significantly different boiling points.

BACKGROUND ART

Due to the exhaustion of traditional energy sources together with an increase in the global energy demand, impetus is currently being given to the development of alternative energy sources. Among them, biomass is renewable quantitative biological resource that attracts a great deal of attention.

Among biomass-based industrial raw materials, isosorbide ($C_6H_{10}O_4$) that is prepared by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide may be used as an additive that can make plastic materials stronger and tougher, and that is also used as an agent for treating cardiac diseases by being boded to nitrate.

When D-glucose obtained from biomass by pretreatment is hydrogenated in the presence of a catalyst, sorbitol is produced. Isosorbide is produced by double dehydration of sorbitol. This cyclization reaction is influenced by various reaction conditions, including temperature, pressure, solvent, catalyst, etc.

Technologies of removing water using vacuum reactions or azeotropic solvents are mainly known. As a technology of removing water under a vacuum, U.S. Pat. No. 7,649,099 discloses a process of producing isosorbide using two reactors including a first reactor and a second reactor, wherein a heterogeneous solid catalyst is introduced into the first reactor and a homogeneous catalyst is introduced into the second reactor and wherein a reaction is carried out at a controlled temperature under a vacuum. However, the above US patent has a disadvantage in that, because the two reactors are used, the investment for the vacuum reaction process is high. Meanwhile, a technology that uses an azeotropic solvent is disclosed in U.S. Pat. No. 6,639,067. The latter US patent discloses a process in which anhydrosugar alcohol is produced by dehydration in the presence of an acid catalyst and an organic solvent, and then separated by azeotropic distillation. However, the process disclosed therein has disadvantages in that it is difficult to control the reaction temperature, because a single azeotropic solvent is used, and in that the reaction temperature is determined according to the boiling point of the solvent used.

Thus, there is a need for a method capable of more efficiently controlling the reaction temperature, unlike the method that uses the single azeotropic solvent.

Accordingly, the present inventors have found that, when a solvent comprising at least two components that form an azeotrope with water and that have significantly different boiling points is used in a process that produces isosorbide from sorbitol, the reaction temperature can be efficiently controlled and the yield of isosorbide can be increased, thereby completing the present invention.

SUMMARY OF INVENTION

It is an object of the present invention to provide a method for producing anhydrosugar alcohol, which can increase the yield of anhydrosugar alcohol by use of at least two azeotropic solvents in an atmospheric pressure reaction that produces anhydrosugar alcohol from sugar alcohol by dehydration.

DETAILED DESCRIPTION OF THE INVENTION

To achieve the above object, the present invention provides a method for producing anhydrosugar alcohol, comprising the steps of:

(a) dehydrating a sugar alcohol in the presence of a first solvent and a second solvent, which form an azeotrope with water, and an acid catalyst, by heating to a temperature at which a solvent mixture of the first solvent and the second solvent is refluxed; and (b) removing a portion of the solvents, and then carrying out an additional dehydration reaction at a temperature of about 120° C. to 180° C., wherein a mixture of water produced during the reaction and evaporated solvents is liquefied, followed by removal of the water and recycling of the solvents.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

The method of the present invention, which comprises removing produced water using azeotropic distillation solvents, uses a solvent mixture that forms an azeotrope with water and that comprises at least two components having significantly different boiling points, unlike conventional technologies. Thus, the method of the present invention can efficiently control the reaction temperature, unlike a method that uses a single solvent, and it can increase the yield of isosorbide in a reaction process that uses azeotropic distillation solvents.

In addition, unlike a conventional technology that uses two reactors, the method of the present invention can efficiently control the reaction temperature even when only one reactor is used, and it is a process in which water is removed at atmospheric pressure. Thus, the method of the present invention makes it possible to reduce investment costs.

Therefore, in one aspect, the present invention is directed to a method for producing anhydrosugar alcohol, comprising the steps of:

(a) dehydrating a sugar alcohol in the presence of a first solvent and a second solvent, which form an azeotrope with water, and an acid catalyst, by heating to a temperature at which a solvent mixture of the first solvent and the second solvent is refluxed; and (b) removing a portion of the solvents, and then carrying out an additional dehydration reaction at a temperature of 120° C. to 180° C., wherein a mixture of water produced during the reaction and evaporated solvents is liquefied, followed by removal of the water and separation of the solvents.

When the evaporated solvent/water mixture resulting from step (a) is liquefied, it is separated into an organic layer and an aqueous layer, and thus the water can be removed and the solvents can be recycled into the reactor and used in the reaction. In addition, when the evaporated solvent/water mixture resulting from step (b) is liquefied, it is separated into an organic layer and an aqueous layer, and thus the water can be removed and the solvents can be recycled into the reactor and used in the reaction. Namely, the reactions in both steps (a) and (b) are carried out under reflux at different reaction temperatures, and the evaporated water/solvent mixture is liquefied to remove the water and to recycle the solvents into the reactor.

The method of the present invention may further comprise step (c) of neutralizing a reaction product resulting from step (b), and distilling the neutralized reaction product under reduced pressure to remove water and the solvents and to recover the anhydrosugar alcohol. In addition, a mixture of water produced during the reaction and evaporated solvents may be liquefied, and after liquefaction, the water may be removed, and then the solvents may be recycled into the reactor and reused in step (a).

In the step of recovering the anhydrosugar alcohol, the solution remaining after neutralization is separated into an organic solvent layer and an aqueous layer. Thus, the organic layer may be recycled into the reactor, and only the aqueous layer may be distilled to recover the anhydrosugar alcohol.

The reaction temperature in step (b) may be about 120° C. to 180° C., preferably about 125° C. to 160° C. If the reaction temperature is lower than 120° C., there will be a problem in that the reaction rate is very low, and if the reaction temperature is higher than 180° C., there will be a problem in that the production of by-products such as a polymer or cokes increases.

The boiling point of the first solvent is lower than that of the second solvent. Preferably, the first solvent is a hydrocarbon having a boiling point of about 60° C. to 120° C., and may be selected from the group consisting of hexane, heptane, cyclohexane, isooctane, benzene, toluene, and a mixture thereof, but is not limited thereto.

The second solvent is a hydrocarbon having a boiling point of about 130° C. to 180° C., and may be selected from the group consisting of ethylbenzene, xylene, cumene, and a mixture thereof, but is not limited thereto.

The boiling points of solvents that can be used as the first solvent and the second solvent are summarized in Table 1 below.

TABLE 1

| First solvent | Boiling point (° C.) | Second solvent | Boiling point (° C.) |
| --- | --- | --- | --- |
| Hexane | 69 | Ethyl benzene | 136.2 |
| Heptane | 79 to 98 | Xylene | 144 |
| Cyclohexane | 80.7 | Cumene | 152 |
| Isooctane | 99.1 to 99.5 | | |
| Benzene | 80.1 | | |
| Toluene | 110.8 | | |

The first solvent that is used in the present invention may be added in an amount of 5-500 parts by weight, preferably 10-200 parts by weight, based on 100 parts by weight of the sugar alcohol. If the first solvent is added in an amount of less than 5 parts by weight, there will be a problem in that the efficiency of removal of water produced during the reaction is low, and thus the reaction rate is low, and if the first solvent is added in an amount of more than 500 parts by weight, there will be a problem in that the efficiency of the reactor is reduced, because the volume of the solvent is large.

The second solvent that is used in the present invention may be added in an amount of 5-500 parts by weight, preferably 10-300 parts by weight, based on 100 parts by weight of the sugar alcohol. If the second solvent is added in an amount of less than 5 parts by weight, there will be a problem in that the efficiency of removal of water produced during the reaction is low, and thus the reaction rate is low, and if the first solvent is added in an amount of more than 500 parts by weight, there will be a problem in that the efficiency of the reactor is reduced, because the volume of the solvent is large.

If the first solvent and the second solvent are used as a mixture, the mixing ratio therebetween may be 1:10 to 10:1. Furthermore, a third solvent may be added to the first solvent and the second solvent to more efficiently control the reaction temperature. The third solvent that is used in the present invention may have a boiling point between the boiling point of the first solvent and the boiling point of the second solvent or may have a boiling point similar to or higher than the boiling point of the second solvent. Examples of the third solvent include n-octane, propylbenzene, trimethyl benzene, ethyl toluene, butylbenzene, isobutyl benzene, nonane, decane and the like, but is not limited thereto.

The temperature at which the solvent mixture is first refluxed may be about 90° C. to 130° C., preferably about 100° C. to 125° C. If the reaction temperature (reflux temperature) is lower than 90° C., there will be a problem in that the reaction rate is very low, and if the reaction temperature is higher than 130° C., there will be a problem in that the yield is reduced due to low reaction selectivity.

In the present invention, the sugar alcohol may be hexitol. Specifically, it may be one or more selected from the group consisting of sorbitol, mannitol and iditol. Preferably, the sugar alcohol is sorbitol. The anhydrosugar alcohol may be isosorbide, isomannide, isoidide or the like. Preferably, the anhydrosugar alcohol is isosorbide.

In addition, the method for producing anhydrosugar alcohol according to the present invention may further comprise, after producing the anhydrosugar alcohol, a step of separating and/or purifying the product. The step of separating and/or purifying the product may be performed using distillation, crystallization and adsorption processes alone or in combination of two or more.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1

70 g of sorbitol, 45 g of heptane, 51 g of xylene and 0.7 g of $H_2SO_4$ were introduced into a 250 cc reactor and allowed to react with stirring for 1 hour by heating to a temperature at which the solvent mixture would be refluxed (110° C.). Then, a portion of the solvents was removed by distillation to control the reaction temperature to a temperature of 132° C. to 135° C., and an additional reaction was carried out at the controlled temperature for 2 hours and 30 minutes. A mixture of water produced during the reaction and evaporated solvent was liquefied in a Dean Stark column. Next, the water was removed, and then the solvents were recycled into the reactor. After completion of the reaction, the reaction product was neutralized with an aqueous NaOH solution. The neutralized reaction product was first distilled under reduced pressure to remove water and the reaction solvents, and then distilled under the conditions of pressure of 10 mmHg and temperature of 160° C. to 230° C. to recover the product.

After the completion of the reaction, the obtained reaction product was diluted 20-fold with water and analyzed by high-performance liquid chromatography (HPLC, Agilent; equipped with a carbohydrate column). The yield of the isosorbide produced was 76.3 mol %.

Example 2

70 g of sorbitol, 45 g of toluene, 51 g of xylene and 0.7 g of $H_2SO_4$ were introduced into a 250 cc reactor and allowed to react with stirring for 1 hour by heating to a temperature at which the solvent mixture would be refluxed (120° C.). Then, a portion of the solvents was removed by distillation to control the reaction temperature to a temperature of 133° C. to 134° C., and an additional reaction was carried out at the controlled temperature for 2 hours and 30 minutes. Removal of water produced during the reaction, and neutralization and distillation processes, were performed in the same manner as described in Example 1.

After the completion of the reaction, the obtained reaction product was diluted 20-fold with water and analyzed by high-performance liquid chromatography (HPLC, Agilent; equipped with a carbohydrate column). The yield of the isosorbide produced was 74.9 mol %.

Example 3

70 g of sorbitol, 20 g of cyclohexane, 70 g of xylene and 0.7 g of $H_2SO_4$ were introduced into a 250 cc reactor and allowed to react with stirring for 1 hour by heating to a temperature at which the solvent mixture would be refluxed (105° C.). Then, a portion of the solvents was removed by distillation to control the reaction temperature to a temperature of 133° C. to 135° C., and an additional reaction was carried out at the controlled temperature for 2 hours and 30 minutes. Removal of water produced during the reaction, and neutralization and distillation processes, were performed in the same manner as described in Example 1.

After the completion of the reaction, the obtained reaction product was diluted 20-fold with water and analyzed by high-performance liquid chromatography (HPLC, Agilent; equipped with a carbohydrate column). The yield of the isosorbide produced was 75.2 mol %.

Comparative Example 1

70 g of sorbitol, 90 g of xylene and 0.7 g of $H_2SO_4$ were introduced into a 250 cc reactor and allowed to react with stirring for 2 hours and 30 minutes by heating to a temperature at which the xylene would be refluxed (139° C. to 141° C.). Removal of water produced during the reaction, and neutralization and distillation processes, were performed in the same manner as described in Example 1.

After the completion of the reaction, the obtained reaction product was diluted 20-fold with water and analyzed by high-performance liquid chromatography (HPLC, Agilent; equipped with a carbohydrate column). The yield of the isosorbide produced was 67.5 mol %.

The yields of the products obtained in Examples 1 to 3 and Comparative Example 1 were calculated using the following equation, and the results of the calculation are shown in Table 2 below:

$$\text{Yield} = [\text{number of moles of isosorbide produced} / \text{number of moles of sorbitol introduced}] \times 100$$

TABLE 2

| | solvents | Temperature and time | Yield of products (mol %) |
|---|---|---|---|
| Example 1 | Heptane/Xylene | 110° C., 1 h --> 132-135° C., 2.5 h | 76.3 |
| Example 2 | Toluene/Xylene | 120° C., 1 h --> 133-134° C., 2.5 h | 74.9 |
| Example 3 | Cyclohexane/Xylene | 105° C., 1.5 h --> 133-135° C., 2.5 h | 75.2 |
| Comp. ex. 1 | Xylene | 139-141° C., 3 h | 67.5 |

As shown in Table 2 above, Examples 1 to 3 of the present invention, in which the reaction temperature was controlled using the solvent mixture that form an azeotrope with water at atmospheric pressure, showed a significant increase in the yield of isosorbide compared to that in the Comparative Example.

INDUSTRIAL APPLICABILITY

As described above, the method for producing anhydrosugar alcohol according to the present invention can increase the yield of anhydrosugar alcohol. In addition, the method of the present invention can efficiently control the reaction temperature through the use of only one reactor, and it is a process in which water is removed at atmospheric pressure. Thus, the method of the present invention makes it possible to reduce investment costs.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing anhydrosugar alcohol, the method comprises:
   (a) dehydrating a sugar alcohol in the presence of a first solvent and a second solvent, both of which form an azeotrope with water, and an acid catalyst, by heating to a temperature at which a solvent mixture of the first solvent and the second solvent is refluxed; and
   (b) removing a portion of the solvents, and then carrying out an additional dehydration reaction at a temperature of 120° C. to 180° C., and liquefying a mixture of water produced during the reaction and evaporated solvents mixture, followed by removal of the water and separation of the solvents,
   wherein a boiling point of the first solvent is lower than that of the second solvent, and the first solvent is a hydrocarbon having a boiling point of 60° C. to 99.5° C.

2. The method of claim 1, further comprising (c) neutralizing a reaction product produced in step (b), and then distilling the reaction product under reduced pressure to remove water and the solvents, and to recover the anhydrosugar alcohol.

3. The method of claim 1, further comprising (c) separating an aqueous layer only from a reaction product produced in step (b) and neutralizing the aqueous layer, and then distilling the aqueous layer under reduced pressure to remove water and to recover the anhydrosugar alcohol.

4. The method of claim 1, wherein the solvents separated in step (b) are recovered and recycled in step (a).

5. The method of claim 1, wherein the first solvent is selected from the group consisting of hexane, heptane, cyclohexane, isooctane, benzene, and a mixture thereof.

6. The method of claim 1, wherein the second solvent is a hydrocarbon having a boiling point of 130° C. to 180° C.

7. The method of claim 1, wherein the second solvent is selected from the group consisting of ethylbenzene, xylene, cumene, and a mixture thereof.

8. The method of claim 1, wherein a third solvent is added to the first solvent and the second solvent.

9. The method of claim 1, wherein a temperature at which the solvent mixture is refluxed is 90° C. to 130° C.

10. The method of claim 1, wherein the anhydrosugar alcohol is isosorbide, and the sugar alcohol is sorbitol.

11. The method of claim 2, wherein a third solvent is added to the first solvent and the second solvent.

12. The method of claim 2, wherein the solvents separated in steps (b) and (c) are recovered and recycled in step (a).

13. The method of claim 3, wherein the solvents separated in steps (b) and (c) are recovered and recycled in step (a).

14. The method of claim 1, wherein the boiling point of the first solvent is 69° C. to 99.5° C.

* * * * *